United States Patent [19]

Maender et al.

[11] 4,342,705

[45] Aug. 3, 1982

[54] METHYLENE THIOETHERS

[75] Inventors: Otto W. Maender; Eiichi Morita, both of Copley, Ohio

[73] Assignee: Monsanto Company, St. Louis, Mo.

[21] Appl. No.: 238,891

[22] Filed: Dec. 1, 1980

Related U.S. Application Data

[62] Division of Ser. No. 97,089, Nov. 23, 1980, Pat. No. 4,271,050.

[51] Int. Cl.³ .............. C07C 149/415; C07C 149/40; C07C 149/41; C07C 149/26
[52] U.S. Cl. .......................... 260/465 D; 260/239 B; 260/326.62; 260/464; 260/465.4; 544/159; 546/226; 546/245; 560/15; 560/17; 560/125; 560/152; 560/154; 564/154; 564/162; 564/189; 564/191; 564/200; 568/42; 568/43
[58] Field of Search ............... 260/464, 465.4, 465 D, 260/326.62, 239 B; 564/154, 162, 189, 191, 200; 568/42, 43; 560/15, 17, 125, 152, 154; 546/226, 245; 544/159

[56] References Cited

U.S. PATENT DOCUMENTS 3,546,185 12/1970 Coran et al. ...................... 260/79.5
3,780,001 12/1973 Son .................................... 260/79.5

OTHER PUBLICATIONS

Chemical Reviews, 1978, vol. 78, No. 4. Barry M. Trost, "α-Sulfenylated Carbonyl Compounds in Organic Synthesis," pp. 363-381.
J. Org. Chem., vol. 42, No. 10, 1977, Field and Chu, "Organic Disulfides and Related Substances, 40, Reactions of Disulfides with Sulfur Ylides", pp. 1768-1773.
J. Applied Polymer Science, vol. 16, 1972, "Some Observations on the Mechanism of Action of Retarders in Rubber Vulcanization, A New Class of Retarder", pp. 2647-2655.
J. Org. Chem., vol. 34, No. 11, pp. 3618-3624 (1969), Russell and Ochrymowycz.
Bulletin of the Chemical Society of Japan, vol. 45, (1972), pp. 866-870, "Sulfenylation of Active Methylene Compounds with Sulfenamides".
Bulletin of the Chemical Society of Japan, vol. 52(4), (1979), pp. 1139-1142, "Interactions Between Sulfur Ylides and Electrophilic Monosulfides".
Chemical & Pharmaceutical Bulletin, vol. 17, No. 3, (1969), "Studies on Antitumor Substances, IX. Chemical Behaviors of Thiosulfonate Toward Active Methylene Compound", pp. 420-424.
Tetrahedron Letters No. 59, 1970, "The Sulfenylation of the Active Methylene Compounds by the Use of Sulfenamides", pp. 5115-5118.

Primary Examiner—Dolph H. Torrence
Attorney, Agent, or Firm—Larry R. Swaney

[57] ABSTRACT

Vulcanizable rubber compositions are described which are inhibited from premature vulcanization by activated methylene di(thioethers) in which the adjacent activating groups are either carbonyl or cyano. Novel compounds are also described.

25 Claims, No Drawings

METHYLENE THIOETHERS

This is a division, of application Ser. No. 097,089, filed Nov. 23, 1980, U.S. Pat. No. 4,271,050.

This invention relates to improved vulcanizable rubber compositions inhibited from premature vulcanization by active methylene thioethers and to certain novel active methylene thioethers.

BACKGROUND OF THE INVENTION

Sulfenamide inhibitors are especially potent for vulcanizable rubber compositions containing sulfenamide accelerators but are less effective when the accelerator is 2-mercaptobenzothiazole or bis-2-benzothiazolyl disulfide. Acid retarders reduce scorchiness of benzothiazole accelerated stocks by adversely affecting both the cure rate and the extent of cure. A study of the mechanism of retarders in rubber vulcanization lead to a class of retarders consisting of hydrocarbylthio derivatives of trialkylsulfonyl methane, J. Appl. Poly. Sci., Vol. 16, pages 2647-2655 (1972), however, these retarders have not gained acceptance. Therefore, there is a need for more effective inhibitors for benzothiazole accelerated stocks.

SUMMARY OF THE INVENTION

It has now been discovered that vulcanizable rubber compositions are protected from premature vulcanization by di(thioethers) derived from activated methylene compounds in which the adjacent activating groups are either carbonyl or cyano. Thus, the inhibitors of the invention are either α,α-gem-disulfenated ketones or α,α-gem-disulfenated nitriles. The two activating groups adjacent to the methylene group may be two carbonyl groups, two cyano groups, or one carbonyl group and one cyano group.

Vulcanizable compositions of the invention comprise sulfur-vulcanizable rubber, sulfur-vulcanizing agent, organic vulcanization accelerating agent and, in an amount effective to inhibit premature vulcanization, a di(thioether) of the formulas

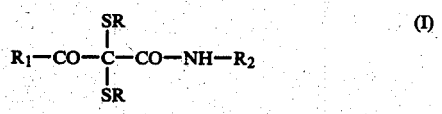

in which R is alkyl of 1-20 carbon atoms, cycloalkyl of 5-12 carbon atoms, benzyl, α-methylbenzyl, phenyl, or substituted phenyl wherein the substituents are lower alkyl, lower alkoxy, or halo, $R_1$ is R or anilino or substituted anilino wherein the substituents are lower alkyl, lower alkoxy or halo, $R_2$ is phenyl or substituted phenyl as above,

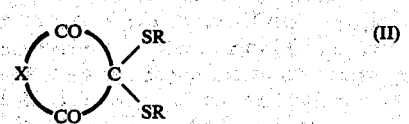

in which R is the same as above and X is o-phenylene or straight or branched alkylene, of 2-4 chain carbon atoms,

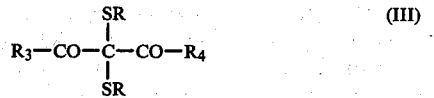

in which R is the same as above, $R_3$ is lower alkyl or lower alkoxy, and $R_4$ is carboalkoxy of 1-5 carbon atoms or

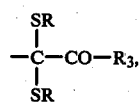

or $R_4$ may be lower alkyl provided that the vulcanization accelerating agent is 2-mercaptobenzothiazole, and

in which R is the same as above and $R_5$ is cyano, carboalkoxy of 1-5 carbon atoms, substituted carbamoyl of the formula

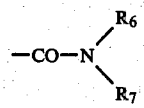

in which $R_6$ is hydrogen or R, $R_7$ is R or carboalkoxy of 1-5 carbon atoms, or $R_6$ and $R_7$ together is alkylene or oxydialkylene of 4-8 carbon atoms which along with the nitrogen atom forms a heterocycle, or $R_5$ may be carbamoyl provided that the vulcanization accelerating agent is 2-mercaptobenzothiazole.

As indicated by the above provisos, inhibitors of Formula (III) wherein $R_4$ is lower alkyl and inhibitors of Formula (IV) wherein $R_5$ is unsubstituted carbamoyl are potent inhibitors when the accelerating agent is 2-mercaptobenzothiazole but are less effective and require high loadings to inhibit premature vulcanization of compositions containing other accelerators, for example, sulfenamide accelerators. This contrasts with the inhibitors of Formula (I) and (II) and the remaining inhibitors of Formulas (III) and (IV) which exhibit inhibitor activity at conventional loadings with all ordinary organic accelerating agents for sulfur vulcanization.

The term "lower" when referring to alkyl or alkoxy means a radical containing 1-5 carbon atoms. Preferred inhibitors of Formula (I) are derived from acetoacetanilide or α-benzoylacetanilide. Preferred inhibitors of Formula (II) are derived from 1,3-cyclohexanedione or 5,5-dialkyl-1,3-cyclohexanedione. More preferred inhibitors are compounds in which R is phenyl. Preferred inhibitors of Formula (IV) are compounds in which $R_5$ is cyano, carbethoxy, carbomethoxy, carbethoxycarbamoyl or carbomethoxycarbamoyl.

Examples of satisfactory radicals for R are methyl, ethyl, propyl, isopropyl, n-butyl, sec.-butyl, isobutyl, pentyl, sec.-pentyl (1-methylbutyl), hexyl, heptyl, octyl, nonyl, decyl, dodecyl, eicosyl, cyclopentyl, cyclohexyl, 2-methylcyclohexyl, 4-methylcyclohexyl, cycloheptyl, cyclooctyl, cyclodecyl, cyclododecyl, 2-methylphenyl, 3-methylphenyl, 4-methylphenyl, 2-methyl-4-t-butylphenyl, 4-t-butylphenyl, 2,4,6-trimethylphenyl, 3-isopropylphenyl, 4-methoxyphenyl, 4-ethoxyphenyl, 4-chlorophenyl, and 2,4-dichlorophenyl. Hydrocarbon radicals are preferred. Preferred alkyl radicals are primary or secondary lower alkyl radicals of 1–5 carbon atoms.

Examples of satisfactory radicals for

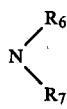

are methylamino, ethylamino, propylamino, isopropylamino, butylamino, t-butylamino, cyclohexylamino, benzylamino, anilino, dimethylamino, diethylamino, dipropylamino, dicyclohexylamino, diphenylamino, pyrrolidinyl, piperidino, morpholino, 2,6-dimethylmorpholino, and hexahydro-1H-azepine-1-yl.

The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions containing a sulfur vulcanizing agent such as an amine disulfide or a polymeric polysulfide but preferably, the vulcanizing agent is elemental sulfur (usually about 0.5–5 parts by weight of sulfur are used per 100 parts by weight of rubber). Rubber compositions containing organic accelerating agents are particularly improved by the inhibitors of the invention with compositions containing 2-mercaptobenzothiazole accelerator being preferred. Any organic accelerating agent in an amount effective (generally about 0.1–5 parts by weight accelerator per 100 parts by weight rubber) to accelerate the sulfur vulcanization of rubber is satisfactory in the practice of this invention. The inhibitors of the invention are effective with any sulfur-vulcanizable natural and synthetic rubber and mixtures thereof. Suitable accelerators and rubbers are described in U.S. Pat. No. 3,546,185, Col. 9, lines 53–75, Col. 10, lines 15–21, and U.S. Pat. No. 3,780,001, Col. 4, lines 43–72, Col. 5, lines 5–33, respectively, the disclosures of which are incorporated herein by reference. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 parts of inhibitor per 100 parts rubber being commonly used. Methods for determining scorch times and curing characteristics of rubber stocks used in illustrating this invention are described in U.S. Pat. No. 3,546,185, Col. 13, lines 30–53. Stress-strain properties are reported in megapascals (MPa).

One embodiment of the invention concerns novel compounds of the formulas

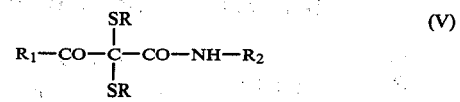

in which R is alkyl of 1–20 carbon atoms, cycloalkyl of 5–12 carbon atoms, benzyl, α-methylbenzyl, phenyl, or substituted phenyl wherein the substituents are lower alkyl, lower alkoxy, or halo, $R_1$ is R or anilino or substituted anilino wherein the substituents are lower alkyl, lower alkoxy or halo, $R_2$ is phenyl or substituted phenyl as above,

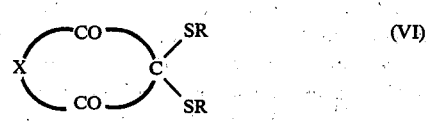

in which R is the same as above and X is o-phenylene or straight or branched alkylene of 2–4 chain carbon atoms,

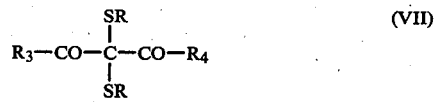

in which R is the same as above, $R_3$ is lower alkyl or lower alkoxy and $R_4$ is carboalkoxy of 1–5 carbon atoms or

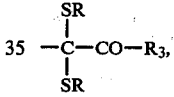

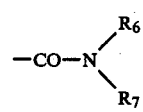

in which R is the same as above and $R_5$ is carboalkoxy of 1–5 carbon atoms, substituted carbamoyl of the formula $$-CO-N\begin{matrix}R_6\\R_7\end{matrix}$$

in which $R_6$ is hydrogen or R, $R_7$ is R or carboalkoxy of 1–5 carbon atoms, or $R_6$ and $R_7$ together is alkylene or oxydialkylene of 4–8 carbon atom which along with the nitrogen atom forms a heterocycle. In preferred compounds of Formula (V), $R_1$ is methyl or phenyl and $R_2$ is phenyl. In preferred compounds of Formula (VIII), $R_5$ is carboalkoxy or carboalkoxycarbamoyl. In more preferred compounds R is phenyl.

Certain inhibitors of the invention are known, for example, 3,3-diphenylthio-2,4-pentanedione and 2,2-diphenylthiomalononitrile are described in *Bulletin of the Chemical Society of Japan*, Vol. 45, 866–870 (1972). The synthesis methods described therein are suitable for preparing inhibitors of this invention. Alternatively, the inhibitors of the invention may be prepared by reacting a sulfenyl chloride with the appropriate active methylene compound. Preferably, the reaction is carried out in the presence of an acid acceptor such as triethylamine, pyridine, and piperidine. Examples of suitable active methylene compounds useful as intermediates are acetoacetanilide (N-phenyl-3-oxobutaneamide), benzoylacetanilide, bis(phenylcarbamoyl)methane, 1,3-cyclohexanedione, indandione, methylacetoacetate, diethyloxalacetate or sodium salt thereof, 2-cyanoacetamide, ethyl cyanoacetate, N-cyanoacetylurethane (ethyl-N-cyanoacetylcarbamate), N-methyl-2-cyanoacetamide, and 2-cyanoacetanilide. Other suitable intermediates are 1-cyanoacetylpyrrolidine, N-phenyl-3-oxo-pentaneamide, 2,4-pentanedione, 2,4-hexanedione, 3,5-heptanedione, 1,3-cyclopentanedione, 1,3-cycloheptanedione, 4-methylindandione, 5-methylindandione, ethylacetoacetate, propylacetoacetate, dimethyloxalacetate (dimethyl-2-oxo-butanedioate), dipropyloxalacetate, methyl cyanoacetate, propyl cyanoacetate, N-cyclohexylcyanoacetamide, 4-(cyanoacetyl)morpholine, N,N-dimethylcyanoacetamide, N,N-diphenylcyanoacetamide, N-methyl-N-phenylcyanoacetamide, 1-cyanoacetylpiperidine, methyl N-cyanoacetylcarbamate, propyl N-cyanoacetylcarbamate, bis(N-methylcarbamoyl)methane and dimethyl 1,3-acetonedicarboxylate.

Examples of inhibitors of the invention are α-acetyl-α,α-di(benzylthio)acetanilide, α-acetyl-α,α-di(butylthio) acetanilide, α-acetyl-α,α-di(cyclohexylthio)acetanilide, bis (phenylcarbamoyl)bis(isopropylthio)methane, bis(phenylcarbamoyl)bis(cyclohexylthio)methane, 2,2-di(phenylthio)-1,3-cyclopentanedione, 2,2-di(phenylthio)-1,3-cycloheptanedione, 2,2-di(isopropylthio)-1,3-cyclopentanedione, 2,2-di(isopropylthio)-1,3-cycloheptanedione, 2,2-di(cyclohexylthio)-indandione, 2,2-di(isopropylthio)-indandione, 2,2-di(phenylthio)-N-phenyl-3-oxo-pentaneamide, 2,2-di(isopropylthio)-N-phenyl-3-oxo-pentaneamide, 2,2-di(cyclohexylthio)-N-phenyl-3-oxopentaneamide, 2,2-di(benzylthio)-1,3-cyclohexanedione, bis (phenylcarbamoyl)-bis(benzylthio)methane, 3,3-di(isopropylthio)-2,4-pentanedione, 3,3-di(phenylthio)-2,4-hexanedione, 4,4-di(-phenylthio)-3,5-heptanedione, 2,2-di(benzylthio)indandione, 2,2-di(phenylthio)-4-methylindandione, 2,2-di(phenylthio)-5-methylindandione, ethyl α-acetyl-α,α-di(isopropylthio) acetate, propyl α-acetyl-α,α-di(isopropylthio)acetate, dimethyl 2,2-di(phenylthio)oxalacetate, dipropyl 2,2-di(phenylthio)-oxalacetate, bis(phenylthio)bis(N-methylcarbamoyl)methane, bis(benzylthio)bis(N-methylcarbamoyl)methane, bis(isopropylthio)bis(N-methylcarbamoyl)methane, bis(cyclohexylthio)bis (N-methylcarbamoyl)methane, methyl di(benzylthio)cyanoacetate methyl di(isopropylthio)cyanoacetate, methyl di(cyclohexylthio)-cyanoacetamide, 4-(1,1-di[phenylthio]-1-cyanoacetyl) morpholine, N,N-dimethyl-2,2-di(phenylthio)cyanoacetamide, N,N-diphenyl-2,2-di(isopropylthio)cyanoacetamide, N-methyl-N-phenyl-2,2-di(phenylthio)cyanoacetamide, methyl di(phenylthio)cyanoacetylcarbamate, methyl di(isopropylthio)-N-cyanoacetylcarbamate and dimethyl 1,1,3,3-tetra(isopropylthio)-1,3-acetonedicarboxylate.

PREFERRED EMBODIMENTS

Examples of inhibitors of the invention are prepared by the following typical procedure. A sulfenyl chloride solution is first prepared by conventional procedures by chlorination at about 0° C. of a mercaptan in an appropriate solvent, for example, methylene chloride. A solution containing two molecular equivalents of a sulfenyl chloride is then added at 0°–25° C. with stirring to a solution containing one molecular equivalent of an active methylene compound, 2.2 molecular equivalents of an acid acceptor, for example, triethylamine, and an appropriate solvent, for example, methylene chloride. The reaction mixture is then stirred for 30–60 minutes. Recovery and purification of the product are conventional. The reaction mixture is then washed with water to remove amine salt by-product. In the case of insoluble products, the solid product is then recovered by filtration. In the case of soluble products, the organic layer is dried over sodium sulfate, filtered and the filtrate is evaporated to recover the product. The product is then recrystallized from an appropriate solvent, for example, ethanol. Identification of the products is confirmed by one or more analyses consisting of elemental, infrared and nuclear magnetic spectral analyses.

Compounds prepared in this manner are tabulated as examples 1–32 in Tables 1–4.

TABLE 1

$$R_1-CO-\underset{\underset{SR}{|}}{\overset{\overset{SR}{|}}{C}}-CO-NH-R_2$$

| Example No. | Compound | R | $R_1$ | $R_2$ | m.p. °C. | Sulfur Analysis Calc. | Sulfur Analysis Found |
|---|---|---|---|---|---|---|---|
| 1 | α-acetyl-α,α-di(phenylthio) acetanilide | phenyl | methyl | phenyl | 172–173 | 15.51 | 16.29 |
| 2 | α-acetyl-α,α-di(cyclohexylthio)acetanilide | cyclohexyl | methyl | phenyl | 158–159.5 | 15.24 | 15.81 |
| 3 | α-acetyl-α,α-di(isopropylthio)acetanilide | isopropyl | methyl | phenyl | 118–119 | 19.76 | 19.70 |
| 4 | α-acetyl-α,α-di(methylthio)acetanilide | methyl | methyl | phenyl | 114–115 | 23.50 | 23.80 |
| 5 | α-acetyl-α,α-di(ethylthio) acetanilide | ethyl | methyl | phenyl | 72–73 | — | — |
| 6 | α-acetyl-α,α-di(propylthio)acetanilide | propyl | methyl | phenyl | 83 | 19.26 | 19.70 |
| 7 | α-acetyl-α,α-di(phenylthio)-o-acetanisidide | phenyl | methyl | 2-methoxyphenyl | 68–73 | — | — |
| 8 | α-acetyl-α,α-di(cyclohexylthio)-p-chloroacetanilide | cyclohexyl | methyl | 4-chlorophenyl | 146–147 | — | — |
| 9 | α-acetyl-α,α-di(cyclohexylthio)-p-chloroacetanilide | cyclohexyl | methyl | 4-chlorophenyl | 176–177 | — | — |
| 10 | α-benzoyl-α,α-di(isopropylthio)acetanilide | isopropyl | phenyl | phenyl | 137–138 | 16.55 | 16.35 |
| 11 | α-benzoyl-α,α-di(phenyl- | phenyl | phenyl | phenyl | 226–228 | 13.41 | 14.07 |

TABLE 1-continued

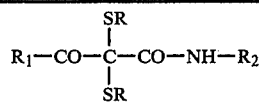

| Example No. | Compound | R | $R_1$ | $R_2$ | m.p. °C. | Sulfur Analysis Calc. | Found |
|---|---|---|---|---|---|---|---|
| | thio)acetanilide | | | | | | |
| 12 | bis(phenylcarbamoyl)bis(phenylthio)methane | phenyl | anilino | phenyl | 198–199 | — | — |

TABLE 2

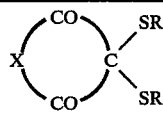

| Example No. | Compound | R | X | m.p. °C. | Sulfur Analysis Calc. | Found |
|---|---|---|---|---|---|---|
| 13 | 2,2-di(phenylthio)-1,3-cyclohexanedione | phenyl | 1,3-propylene | 126–127 | 19.52 | 19.55 |
| 14 | 2,2-di(cyclohexylthio)-1,3-cyclohexanedione | cyclohexyl | 1,3-propylene | 170.5–172 | 18.83 | 18.29 |
| 15 | 2,2-di(isopropylthio)-1,3-cyclohexanedione | isopropyl | 1,3-propylene | 157–158 | — | — |
| 16 | 2,2-di(phenylthio)-5,5-dimethyl-1,3-cyclohexanedione | phenyl | 2,2-dimethyl-1,3-propylene | 160.5–162 | 17.99 | 17.69 |
| 17 | 2,2-di(cyclohexylthio)-5,5-dimethyl-1,3-cyclohexanedione | cyclohexyl | 2,2-dimethyl-1,3-propylene | 191–193 | 17.40 | 16.79 |
| 18 | 2,2-di(phenylthio)-indandione | phenyl | o-phenylene | 126–128 | — | — |

TABLE 3

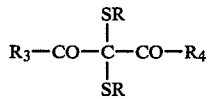

| Example No. | Compound | R | $R_3$ | $R_4$ | m.p. °C. |
|---|---|---|---|---|---|
| 19 | diethyl 2,2-di(phenylthio)oxalacetate | phenyl | ethoxy | carbethoxy | 74–76 |
| 20 | diethyl 2,2-di(isopropylthio)oxalacetate | isopropyl | ethoxy | carbethoxy | liquid |
| 21 | 3,3-di(phenylthio)-2,4-pentanedione | phenyl | methyl | methyl | 119–120 |
| 22 | methyl α,α-di(phenylthio)acetoacetate | phenyl | methoxy | methyl | 75.5–76 |
| 23 | diethyl 1,1,3,3-tetra-(phenylthio)-1,3-acetonedicarboxylate | phenyl | ethoxy | $-\overset{\underset{\mid}{SR}}{\underset{\underset{\mid}{SR}}{C}}-CO-R_3$ | 145–146 |
| 24 | diethyl 1,1,3,3-tetra-(cyclohexylthio)-1,3-acetonedicarboxylate | cyclohexyl | ethoxy | $-\overset{\underset{\mid}{SR}}{\underset{\underset{\mid}{SR}}{C}}-CO-R_3$ | liquid (70% assay) |

TABLE 4

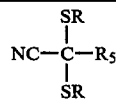

| Example No. | Compound | R | $R_5$ | m.p. °C. | Sulfur Analysis Calc. | Found |
|---|---|---|---|---|---|---|
| 25 | 2,2-di(phenylthio)-2-cyanoacetamide | phenyl | carbamoyl | 151–152 | 21.58 | 21.35 |
| 26 | N-(α,α-[diphenylthio]cyanoacetyl)urethane | phenyl | carbethoxy-carbamoyl | 113–114 | 16.59 | 17.22 |
| 27 | ethyl-di(phenylthio)cyanoacetate | phenyl | carbethoxy | 36 | 19.36 | 19.46 |

TABLE 4-continued $$NC-\underset{\underset{SR}{|}}{\overset{\overset{SR}{|}}{C}}-R_5$$

| Example No. | Compound | R | $R_5$ | m.p. °C. | Sulfur Analysis Calc. | Found |
|---|---|---|---|---|---|---|
| 28 | 2,2-di(phenylthio)-malononitrile | phenyl | cyano | 54–55 | — | — |
| 29 | 1-(α-cyano-α,α-di[phenylthio]acetyl)pyrrolidine | phenyl | pyrrolidinylcarbonyl | 86 | 17.42 | 18.14 |
| 30 | 2,2-di(isopropylthio)-2-cyanoacetamide | isopropyl | carbamoyl | 75 | — | — |
| 31 | 2,2-di(phenylthio)-2-cyanoacetanilide | phenyl | phenylcarbamoyl | 110 | — | — |
| 32 | 2,2-di(isopropylthio)-2-cyanoacetanilide | isopropyl | phenylcarbamoyl | 69–70 | — | — |

The invention is illustrated by incorporating inhibitors of the invention into the following natural rubber masterbatch.

| | Masterbatch |
|---|---|
| Smoked Sheets | 100 |
| Carbon Black | 40 |
| Extender Oil | 10 |
| Wax | 2 |
| Zinc Oxide | 5 |
| Stearic Acid | 1 |
| | 158 |

Vulcanizable compositions are prepared by incorporation of accelerator and sulfur. Compositions of the invention are prepared by incorporating inhibitors in the indicated quantities into the vulcanizable compositions. Compositions containing no inhibitors are controls. The results are shown in Tables 5–12.

In Table 5, the vulcanizable rubber composition comprises 158 parts of natural rubber masterbatch, 2 parts of N-(1,3-dimethylbutyl)-N'-(phenyl)-p-phenylenediamine (Santoflex 13 antidegradant), 0.5 parts of N-(t-butyl)-benzothiazolesulfenamide (Santocure NS accelerator) and 2.5 parts of sulfur. All parts are by weight. Stock 1 is a control containing no inhibitor. Stocks 2–10 contain 1 part of inhibitor.

The data show that α,α-gem-disulfenated derivatives of acetoacetanilide and benzoylacetanilide impart processing safety to the vulcanizable compositions as shown by the increase in scorch delay. The data further indicate that the phenyl and isopropyl compounds exhibit greater activity and that the benzoylacetanilide compound is especially potent.

TABLE 5

| | 1 | 2 | 3 | 4 | 5 | 5 | 7 | 8 | 9 | 10 |
|---|---|---|---|---|---|---|---|---|---|---|
| NR Masterbatch | 158 | → | → | → | → | → | → | → | → | → |
| Santoflex ® 13 Antidegradant | 2 | → | → | → | → | → | → | → | → | → |
| Santocure ® NS Accelerator | 0.5 | → | → | → | → | → | → | → | → | → |
| Sulfur | 2.5 | → | → | → | → | → | → | → | → | → |
| α-acetyl-α,α-di(phenylthio)acetanilide | — | 1 | — | — | — | — | — | — | — | — |
| α-acetyl-α,α-di(cyclohexylthio)acetanilide | — | — | 1 | — | — | — | — | — | — | — |
| α-acetyl-α,α-di(isopropylthio)acetanilide | — | — | — | 1 | — | — | — | — | — | — |
| α-acetyl-α,α-di(methylthio)acetanilide | — | — | — | — | 1 | — | — | — | — | — |
| α-acetyl-α,α-di(propylthio)acetanilide | — | — | — | — | — | 1 | — | — | — | — |
| α-acetyl-α,α-di(ethylthio)acetanilide | — | — | — | — | — | — | 1 | — | — | — |
| α-acetyl-α,α-di(phenylthio)-p-chloroacetanilide | — | — | — | — | — | — | — | 1 | — | — |
| α-acetyl-α,α-di(cyclohexylthio)-p-chloroacetanilide | — | — | — | — | — | — | — | — | 1 | — |
| α-benzoyl-α,α-di(phenylthio)acetanilide | — | — | — | — | — | — | — | — | — | 1 |
| MOONEY SCORCH @ 121° C. | | | | | | | | | | |
| $t_5$, minutes | 28.6 | 51.6 | 44.4 | 53.9 | 38.0 | 41.0 | 42.5 | 48.4 | 45.5 | 68.4 |
| % increase in scorch delay | — | 80 | 55 | 88 | 33 | 43 | 49 | 69 | 59 | 139 |
| STRESS-STRAIN @ 153° C. | | | | | | | | | | |
| $M_{300}$, MPa | 7.5 | 7.3 | 6.9 | 6.7 | 7.3 | 6.7 | 6.7 | 7.1 | 7.3 | 6.4 |
| UTS, MPa | 24.9 | 25.8 | 24.6 | 25.1 | 26.6 | 25.6 | 25.9 | 25.6 | 25.2 | 25.3 |
| Elong., % | 620 | 670 | 630 | 650 | 650 | 670 | 660 | 660 | 650 | 620 |

Vulcanizable compositions containing 2-mercaptobenzothiazole as the vulcanization accelerator are illustrated in Tables 6 and 7. The data show that the inhibitors substantially enhance the scorch safety of the compositions and, in addition, increase the cure rate and the tensile strength. The data of Stocks 5–9 of Table 6 show that the amount of scorch delay is essentially directly proportional to the quantity of inhibitor used.

Vulcanizable rubber compositions containing different accelerators are shown in Table 8. The data indicate that the inhibitor of the invention is especially potent in the composition in which the accelerator is the amine salt of 2-mercaptobenzothiazole.

Inhibitors of the invention derived from cyclic diones are illustrated in Table 9. The data indicate the phenyl derivatives are more active.

Inhibitors of the invention derived from oxalacetate ester, acetoacetate ester, 2,4-pentanedione and indandione are illustrated in Table 10. The data show that the inhibitors exhibit substantial prevulcanization inhibitor activity in compositions in which the accelerator is 2-mercaptobenzothiazole. In other experiments, not shown, $\alpha,\alpha$-di(phenylthio) derivatives of diethyloxalacetate, 2,4-pentanedione, and methylacetoacetate at comparable loadings exhibit little or no activity in vulcanizable rubber compositions containing sulfenamide accelerators.

TABLE 6

|  | 1 | 2 | 3 | 4 | 5 | 6 | 7 | 8 | 9 |
|---|---|---|---|---|---|---|---|---|---|
| NR Masterbatch | 158 | → | → | → | → | → | → | → | → |
| 2-mercaptobenzothiazole | 1 | → | → | → | → | → | → | → | → |
| Sulfur | 2.5 | → | → | → | → | → | → | → | → |
| $\alpha$-acetyl-$\alpha,\alpha$-di(phenylthio)-p-chloroacetanilide | — | 0.855 | — | — | — | — | — | — | — |
| $\alpha$-acetyl-$\alpha,\alpha$-di(cyclohexylthio)-p-chloroacetanilide | — | — | 0.88 | — | — | — | — | — | — |
| $\alpha$-acetyl-$\alpha,\alpha$-di(methylthio)-acetanilide | — | — | — | 0.54 | — | — | — | — | — |
| $\alpha$-acetyl-$\alpha,\alpha$-di(isopropylthio)-acetanilide | — | — | — | — | 0.65 | 1.3 | — | — | — |
| $\alpha$-acetyl-$\alpha,\alpha$-di(phenylthio)-acetanilide | — | — | — | — | — | — | 0.395 | 0.785 | 1.595 |
| Mooney Scorch @ 121° C. | | | | | | | | | |
| $t_5$, minutes | 12.4 | 24.7 | 23.0 | 25.4 | 25.0 | 50.4 | 19.3 | 24.9 | 37.5 |
| % increase in scorch delay | — | 99 | 85 | 105 | 102 | 306 | 56 | 101 | 202 |
| Rheometer @ 153° C. | | | | | | | | | |
| $t_{90}$–$t_2$, min. | 9.6 | 8.3 | 8.5 | 10.1 | 8.8 | 9.0 | 8.5 | 7.9 | 8.9 |
| Stress-Strain @ 153° C. | | | | | | | | | |
| $M_{300}$, MPa | 3.5 | 3.9 | 4.0 | 4.0 | 3.9 | 4.1 | 3.7 | 4.2 | 3.9 |
| UTS, MPa | 17.0 | 19.2 | 19.2 | 19.1 | 19.2 | 20.9 | 17.7 | 20.6 | 21.4 |
| Elong., % | 680 | 690 | 680 | 690 | 690 | 710 | 670 | 700 | 730 |

TABLE 7

|  | 1 | 2 | 3 | 4 | 5 |
|---|---|---|---|---|---|
| NR Masterbatch | 158 | 158 | 158 | 158 | 158 |
| 2-mercaptobenzothiazole | 1 | 1 | 1 | 1 | 1 |
| Sulfur | 2.5 | 2.5 | 2.5 | 2.5 | 2.5 |
| $\alpha$-benzoyl-$\alpha,\alpha$-di(phenylthio)acetanilide | — | 0.91 | — | — | — |
| $\alpha$-acetyl-$\alpha,\alpha$-di(phenylthio)acetanilide | — | — | 0.785 | — | — |
| $\alpha$-acetyl-$\alpha,\alpha$-di(cyclohexylthio)acetanilide | — | — | — | 0.81 | — |
| $\alpha$-acetyl-$\alpha,\alpha$-di(phenylthio)-o-acetanisidide | — | — | — | — | 0.865 |
| Mooney Scorch @ 121° C. | | | | | |
| $t_5$, minutes | 13.5 | 26.1 | 23.7 | 24.9 | 21.5 |
| % increase in scorch delay | — | 93 | 76 | 84 | 59 |
| Rheometer @ 153° C. | | | | | |
| $t_{90}$–$t_2$, min. | 9.5 | 8.5 | 7.9 | 8.2 | 8.1 |
| Stress-Strain @ 153° C. | | | | | |
| $M_{300}$, MPa | 3.7 | 4.3 | 3.9 | 4.2 | 3.9 |
| UTS, MPa | 18.3 | 20.8 | 21.0 | 20.8 | 18.9 |
| Elong., % | 690 | 690 | 710 | 690 | 680 |

TABLE 8

|  | 1 | 2 | 3 | 4 | 5 | 6 | 7 | 8 | 9 | 10 |
|---|---|---|---|---|---|---|---|---|---|---|
| NR Masterbatch | 158 | → | → | → | → | → | → | → | → | → |
| Sulfur | 2.5 | → | → | → | → | → | → | → | → | → |
| bis-(dimethylthiocarbamyl) sulfide | 0.5 | 0.5 | — | — | — | — | — | — | — | — |
| 2,2'-bis(dithiobenzothiazole) | — | — | 1 | 1 | — | — | — | — | — | — |
| zinc 0,0'-dibutyl phosphorodithioate | — | — | — | — | 1.5 | 1.5 | — | — | — | — |
| zinc 2-mercaptobenzothiazole | — | — | — | — | — | — | 1 | 1 | — | — |
| tert-butylamine salt of 2-mercaptobenzothiazole | — | — | — | — | — | — | — | — | 0.5 | 0.5 |
| $\alpha$-acetyl-$\alpha,\alpha$-di(phenylthio)acetanilide | — | 0.5 | — | 0.5 | — | 0.5 | — | 0.65 | — | 0.65 |
| Mooney Scorch @ 121° C. | | | | | | | | | | |
| $t_5$, minutes | 17.2 | 30.7 | 21.3 | 28.4 | 23.0 | 43.6 | 17.2 | 35.0 | 10.0 | 29.4 |
| % increase in scorch delay | — | 78 | — | 33 | — | 90 | — | 103 | — | 194 |
| Stress-Strain @ 153° C. | | | | | | | | | | |
| $M_{300}$, MPa | 6.9 | 6.8 | 4.2 | 4.6 | 3.9 | 4.5 | 4.2 | 4.7 | 6.3 | 5.6 |
| TS, MPa | 25.9 | 25.4 | 21.2 | 21.1 | 18.1 | 21.3 | 11.8 | 17.6 | 24.3 | 22.8 |

TABLE 8-continued

|  | 1 | 2 | 3 | 4 | 5 | 6 | 7 | 8 | 9 | 10 |
|---|---|---|---|---|---|---|---|---|---|---|
| Elong., % | 630 | 620 | 690 | 680 | 660 | 690 | 540 | 640 | 650 | 670 |

TABLE 9

|  | 1 | 2 | 3 | 4 | 5 | 6 |
|---|---|---|---|---|---|---|
| NR Masterbatch | 158 | 158 | 158 | 158 | 158 | 158 |
| 2-mercaptobenzothiazole | 1 | 1 | 1 | 1 | 1 | 1 |
| Sulfur | 2.5 | 2.5 | 2.5 | 2.5 | 2.5 | 2.5 |
| 2,2-di(phenylthio)-1,3-cyclohexanedione | — | 0.655 | — | — | — | — |
| 2,2-di(isopropylthio)-1,3-cyclohexanedione | — | — | 0.52 | — | — | — |
| 2,2-di(cyclohexylthio)-1,3-cyclohexanedione | — | — | — | 0.68 | — | — |
| 2,2-di(phenylthio)-5,5-dimethyl-1,3-cyclohexanedione | — | — | — | — | 0.715 | — |
| 2,2-di(cyclohexylthio)-5,5-dimethyl-1,3-cyclohexanedione | — | — | — | — | — | 0.735 |
| Mooney Scorch @ 121° C. | | | | | | |
| $t_5$, minutes | 15.0 | 27.4 | 24.9 | 21.4 | 28.7 | 20.5 |
| % increase in scorch delay | — | 83 | 66 | 43 | 91 | 37 |
| Rheometer @ 153° C. | | | | | | |
| $t_{90}-t_2$, min. | 11.8 | 9.3 | 8.6 | 8.0 | 8.7 | 8.4 |
| Stress-Strain @ 153° C. | | | | | | |
| $M_{300}$, MPa | 3.2 | 3.7 | 4.1 | 4.2 | 4.4 | 4.3 |
| UTS, MPa | 15.0 | 19.3 | 22.8 | 22.8 | 21.0 | 23.1 |
| Elong., % | 690 | 740 | 760 | 750 | 730 | 740 |

TABLE 10

|  | 1 | 2 | 3 | 4 | 5 | 6 | 7 |
|---|---|---|---|---|---|---|---|
| NR Masterbatch | 158 | 158 | 158 | 158 | 158 | 158 | 158 |
| 2-mercaptobenzothiazole | 1 | 1 | 1 | 1 | 0.6 | 0.6 | 0.6 |
| Sulfur | 2.5 | 2.5 | 2.5 | 2.5 | 2.5 | 2.5 | 2.5 |
| Diethyl α,α-di(phenylthio)oxalacetate | — | 0.81 | — | — | — | — | — |
| α,α-diphenylthio-2,4-pentanedione | — | — | 0.635 | — | — | — | — |
| Methyl α,α-di(phenylthio)acetoacetate | — | — | — | 0.66 | — | — | — |
| 2,2-di(phenylthio)indandione | — | — | — | — | 0.65 | — | — |
| Diethyl 2,2-di(isopropylthio)oxalacetate | — | — | — | — | — | — | 0.6 |
| MOONEY SCORCH @ 121° C. | | | | | | | |
| $t_5$, minutes | 13.0 | 27.3 | 21.0 | 20.0 | 7.5 | 14.4 | 12.4 |
| % increase in scorch delay | — | 110 | 62 | 54 | — | 92 | 65 |
| RHEOMETER @ 153° C. | | | | | | | |
| $t_{90}-t_2$, min. | 9.3 | 8.8 | 8.3 | 8.4 | 12.4 | 9.9 | 12.3 |
| STRESS-STRAIN @ 153° C. | | | | | | | |
| $M_{300}$, MPa | 3.4 | 3.8 | 4.0 | 4.1 | 3.6 | 3.7 | 3.3 |
| UTS, MPa | 17.3 | 20.4 | 20.8 | 20.7 | 16.2 | 17.9 | 17.2 |
| Elong., % | 700 | 720 | 700 | 690 | 660 | 680 | 730 |

TABLE 11

|  | 1 | 2 | 3 | 4 | 5 | 6 |
|---|---|---|---|---|---|---|
| NR Masterbatch | 158 | 158 | 158 | 158 | 158 | 158 |
| 2-mercaptobenzothiazole | 1 | 1 | 1 | 1 | 1 | 1 |
| Sulfur | 2.5 | 2.5 | 2.5 | 2.5 | 2.5 | 2.5 |
| 2,2-di(phenylthio)malononitrile | — | 0.565 | — | — | — | — |
| N-(α,α-di[phenylthio]cyanoacetyl)urethane | — | — | 0.745 | — | — | — |
| Ethyl di(phenylthio)cyanoacetate | — | — | — | 0.66 | — | — |
| 2,2-di(phenylthio)-2-cyanoacetamide | — | — | — | — | 0.60 | — |
| 1(α-cyano-α,α-di[phenylthio]acetyl)-pyrrolidine | — | — | — | — | — | 0.705 |
| MOONEY SCORCH @ 121° C. | | | | | | |
| $t_5$, minutes | 13.0 | 32.3 | 34.7 | 28.5 | 24.2 | 21.9 |
| % increase in scorch delay | — | 148 | 167 | 119 | 86 | 68 |
| RHEOMETER @ 153° C. | | | | | | |
| $t_{90}-t_2$, min. | 9.6 | 8.8 | 9.1 | 7.9 | 8.3 | 7.0 |
| STRESS-STRAIN @ 153° C. | | | | | | |
| $M_{300}$, MPa | 3.3 | 3.6 | 3.7 | 3.8 | 3.9 | 4.1 |
| UTS, MPa | 18.2 | 19.5 | 19.2 | 20.6 | 20.3 | 22.1 |
| Elong., % | 710 | 720 | 710 | 730 | 720 | 720 |

TABLE 12

|  | 1 | 2 | 3 | 4 | 5 |
|---|---|---|---|---|---|
| NR Masterbatch | 158 | → | → | → | → |
| 2-mercaptobenzothiazole | 1 | → | → | → | → |

TABLE 12-continued

|  | 1 | 2 | 3 | 4 | 5 |
|---|---|---|---|---|---|
| Sulfur | 2.5 | → | → | → | → |
| 2,2-di(phenylthio)-2-cyanoacetamide | — | 0.6 | — | — | — |
| 2,2-di(isopropylthio)-2-cyanoacetamide | — | — | 0.44 | — | — |
| 2,2-di(phenylthio)-2-cyanoacetanilide | — | — | — | 0.755 | — |
| 2,2-di(isopropylthio)-2-cyanoacetanilide | — | — | — | — | 0.615 |
| MOONEY SCORCH @ 121° C. | | | | | |
| $t_5$, minutes | 11.0 | 21.5 | 23.8 | 19.9 | 22.7 |
| % increase in scorch delay | — | 95 | 116 | 81 | 106 |
| STRESS-STRAIN @ 153° C. | | | | | |
| $M_{300}$, MPa | 5.8 | 5.3 | 5.0 | 5.4 | 5.2 |
| UTS, MPa | 17.7 | 21.1 | 20.3 | 21.2 | 19.0 |
| Elong., % | 570 | 640 | 660 | 650 | 630 |

TABLE 13

|  | 1 | 2 | 3 | 4 | 5 | 6 |
|---|---|---|---|---|---|---|
| NR Masterbatch | 158 | 158 | 158 | 158 | 158 | 158 |
| 2-mercaptobenzothiazole | 0.6 | 0.6 | 0.6 | — | — | — |
| Santocure ® NS Accelerator | — | — | — | 0.6 | 0.6 | 0.6 |
| Sulfur | 2.5 | 2.5 | 2.5 | 2.5 | 2.5 | 2.5 |
| Diethyl 1,1,3,3-tetra(phenylthio)1,3-acetone-dicarboxylate | — | 0.57 | — | — | 0.4 | — |
| Diethyl 1,1,3,3-tetra(cyclohexylthio)-1,3-acetone dicarboxylate | — | — | 0.59 | — | — | 0.4 |
| MOONEY SCORCH @ 135° C. | | | | | | |
| $t_5$, minutes | 5.9 | 11.1 | 6.5 | 13.8 | 21.1 | 13.7 |
| % increase in scorch delay | — | 88 | 10 | — | 53 | — |
| STRESS-STRAIN @ 153° C. | | | | | | |
| $M_{300}$, MPa | 5.2 | 4.8 | 4.7 | 8.7 | 7.2 | 6.8 |
| UTS, MPa | 13.8 | 15.3 | 14.2 | 27.3 | 24.6 | 25.2 |
| Elong., % | 550 | 580 | 560 | 620 | 630 | 640 |

Inhibitors of the invention derived from cyano containing active methylene compounds are illustrated in Tables 11 and 12. The data of Table 11 indicate that the 2,2-di(phenylthio)malononitrile and N-(cyanodi[-phenylthio])-urethane are especially potent. The data of Table 12 show that derivatives of 2-cyanoacetamide and 2-cyanoacetanilide exhibit good activity and that the isopropyl derivatives are better.

Inhibitors derived from diethyl 1,3-acetonedicarboxylate are illustrated in Table 13. Stocks 1–3 contain 2-mercaptobenzothiazole as accelerator. Stocks 4–6 contain a sulfenamide accelerator. Stocks 1 and 4 are controls containing no inhibitor. The data show that the phenylthio derivative is more potent than the corresponding cyclohexylthio derivative.

Similar results are obtained with inhibitors of the invention in vulcanizable compositions comprising synthetic rubber such as styrene-butadiene rubber.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formulas

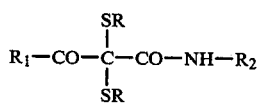 (V)

in which R is alkyl of 1–20 carbon atoms, cycloalkyl of 5–12 carbon atoms, benzyl, α-methylbenzyl, phenyl, or substituted phenyl wherein the substituents are lower alkyl, lower alkoxy, or halo, $R_1$ is R or anilino or substituted anilino wherein the substituents are lower alkyl, lower alkoxy or halo, and $R_2$ is phenyl or substituted phenyl as above, and

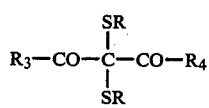 (VI)

in which R is the same as above and X is o-phenylene or straight or branched alkylene of 2–4 chain carbon atoms, and

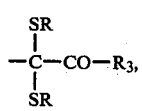 (VII)

in which R is the same as above, $R_3$ is lower alkyl or lower alkoxy, and $R_4$ is carboalkoxy of 1–5 carbon atoms or

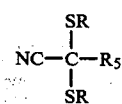

and

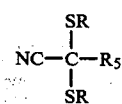 (VIII)

in which R is the same as above and $R_5$ is carboalkoxy of 1–5 carbon atoms, substituted carbamoyl of the formula

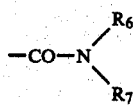

in which $R_6$ is hydrogen or R, $R_7$ is R or carboalkoxy of 1–5 carbon atoms, or $R_6$ and $R_7$ together is alkylene or oxydialkylene of 4–8 carbon atoms which along with the nitrogen atom forms a heterocycle.

2. The compound of claim 1 of Formula (V) in which R is lower alkyl, cyclohexyl, benzyl, or phenyl, $R_1$ is lower alkyl, phenyl, or anilino, and $R_2$ is phenyl.

3. The compound of claim 2 in which $R_1$ is methyl.

4. The compound of claim 2 in which $R_1$ is phenyl.

5. The compound of claim 2 in which $R_1$ is anilino.

6. The compound of claim 3 in which R is isopropyl.

7. The compound of claim 3 in which R is phenyl.

8. The compound of claim 4 in which R is isopropyl.

9. The compound of claim 4 in which R is phenyl.

10. The compound of claim 1 of Formula (VI) in which R is lower alkyl, cyclohexyl, benzyl, or phenyl and X is o-phenylene.

11. The compound of claim 10 in which R is isopropyl.

12. The compound of claim 10 in which R is phenyl.

13. The compound of claim 10 in which X is 1,3-propylene.

14. The compound of claim 13 in which R is isopropyl.

15. The compound of claim 13 in which R is phenyl.

16. The compound of claim 1 of Formula (VII) in which R is lower alkyl, cyclohexyl, benzyl or phenyl, $R_3$ is methoxy or ethoxy, and $R_4$ is carbomethoxy or carbethoxy.

17. The compound of claim 16 in which $R_3$ is ethoxy, $R_4$ is carbethoxy and R is isopropyl.

18. The compound of claim 16 in which $R_3$ is ethoxy, $R_4$ is carbethoxy and R is phenyl.

19. The compound of claim 1 of Formula (VIII) in which R is lower alkyl, cyclohexyl, benzyl, or phenyl and $R_5$ is carboalkoxy.

20. The compound of claim 19 in which $R_5$ is carbethoxy and R is isopropyl.

21. The compound of claim 19 in which $R_5$ is carbethoxy and R is phenyl.

22. The compound of claim 19 in which R is lower alkyl, cyclohexyl, benzyl, or phenyl and $R_5$ is substituted carbamoyl in which $R_6$ is hydrogen and $R_7$ is phenyl or carboalkoxy.

23. The compound of claim 22 in which $R_7$ is phenyl and R is isopropyl.

24. The compound of claim 22 in which R and $R_7$ are phenyl.

25. The compound of claim 22 in which $R_7$ is carbethoxy and R is phenyl.

* * * * *